United States Patent [19]
Nagel et al.

[11] Patent Number: 5,640,707
[45] Date of Patent: Jun. 17, 1997

[54] METHOD OF ORGANIC HOMOLOGATION EMPLOYING ORGANIC-CONTAINING FEEDS

[75] Inventors: Christopher J. Nagel, Wayland, Mass.; Robert D. Bach, Gross Pointe, Mich.

[73] Assignee: Molten Metal Technology, Inc., Waltham, Mass.

[21] Appl. No.: 173,346

[22] Filed: Dec. 23, 1993

[51] Int. Cl.$^6$ .................................................... A62D 3/00
[52] U.S. Cl. ........................................... 588/201; 585/531
[58] Field of Search ............................. 588/201; 585/531

[56] References Cited

U.S. PATENT DOCUMENTS

| | | | |
|---|---|---|---|
| 2,858,255 | 10/1958 | Segui et al. | 202/219 |
| 3,974,206 | 8/1976 | Tatsumi et al. | 260/486 |
| 3,996,022 | 12/1976 | Larsen et al. | 44/1 |
| 4,012,457 | 3/1977 | Bredeson et al. | 260/683 |
| 4,552,667 | 11/1985 | Shultz | 210/757 |
| 4,574,038 | 3/1986 | Wan | 204/162 |
| 4,574,714 | 3/1986 | Bach et al. | 110/346 |
| 4,666,696 | 5/1987 | Shultz | 423/659 |
| 4,769,507 | 9/1988 | Murib et al. | 585/500 |
| 5,177,304 | 1/1993 | Nagel | 588/201 |
| 5,191,154 | 3/1993 | Nagel | 588/201 |

FOREIGN PATENT DOCUMENTS

| | | |
|---|---|---|
| 0 067 491 A2 | 12/1982 | European Pat. Off. . |
| 1618182 | 12/1970 | Germany . |
| 2058553 | 2/1974 | Germany . |
| 44-11648 | 5/1969 | Japan . |
| 936899 | 9/1963 | United Kingdom . |
| 1270074 | 4/1972 | United Kingdom . |
| 1350612 | 4/1974 | United Kingdom . |
| 2088893 | 6/1982 | United Kingdom . |
| 399526 | 9/1993 | United Kingdom . |
| 93/02751 | 2/1993 | WIPO . |

OTHER PUBLICATIONS

Kashiwadate et al., "The Dehydrogenation of Butyl Alcohols by the Molten–metal Catalysts," *Bulletin of the Chemical Society*, 44:3004–3009, (1971).

Saito et al., "Dehydrogenation of Some Alcohols by the Molten Metal Catalyst," *Bulletin of the Japan Petroleum Institute*, 14, No. 2:169–173, (1972).

Adams et al., "Dehydrogenation and Coupling Reactions in the Presence of Iodine and Molten Salt Hydrogen Iodide Acceptors," *Journal of Organic Chemistry*, 42, no. 1:1–6, (1977).

Haggin, J., "Growth and Dissociation of Metal–Carbon Nanocrystals Probed," *Chem. & Eng. News*, pp. 29–32, Oct. 25, 1993.

Haggin, J., "European Conference Draws Attention to Fundamental Role of Catalysis," *Chem & Eng. News*, pp. 26–30, Oct. 18, 1993.

Layman, P.L., "Advances in Feedstock Recycling Offer Help with Plastic Waste," *Chem & Eng. News*, pp. 11–14, Oct. 4, 1993.

Satterfield, C.N., "Acid and Zeolite Catalysts," In Gail F. Nalven (Ed.), *Heterogeneous Catalysis in Industrial Practice*, 2nd Ed., (NY: McGraw–Hill), pp. 209–266, pp. 339–417, (1991).

Jebens, A.M., "CEH Marketing Research Report, Ethylene," *Chemical Economics Handbook–SRI International*, (Report Olefins 432.0000 A) Sep., 1992.

*Primary Examiner*—Ngoclan Mai
*Attorney, Agent, or Firm*—Hamilton, Brook, Smith & Reynolds, P.C.

[57] ABSTRACT

A method includes organic homologation employing an organic-containing feed. The organic-containing feed is directed into a molten metal bath. The molten metal bath includes a metal which can cause an organic component of the organic-containing feed to homologate and form a homologated organic compound. Operating conditions are established and maintained in the reactor to cause the organic component to form a homologated organic compound that is discharged from the molten metal bath.

39 Claims, 1 Drawing Sheet

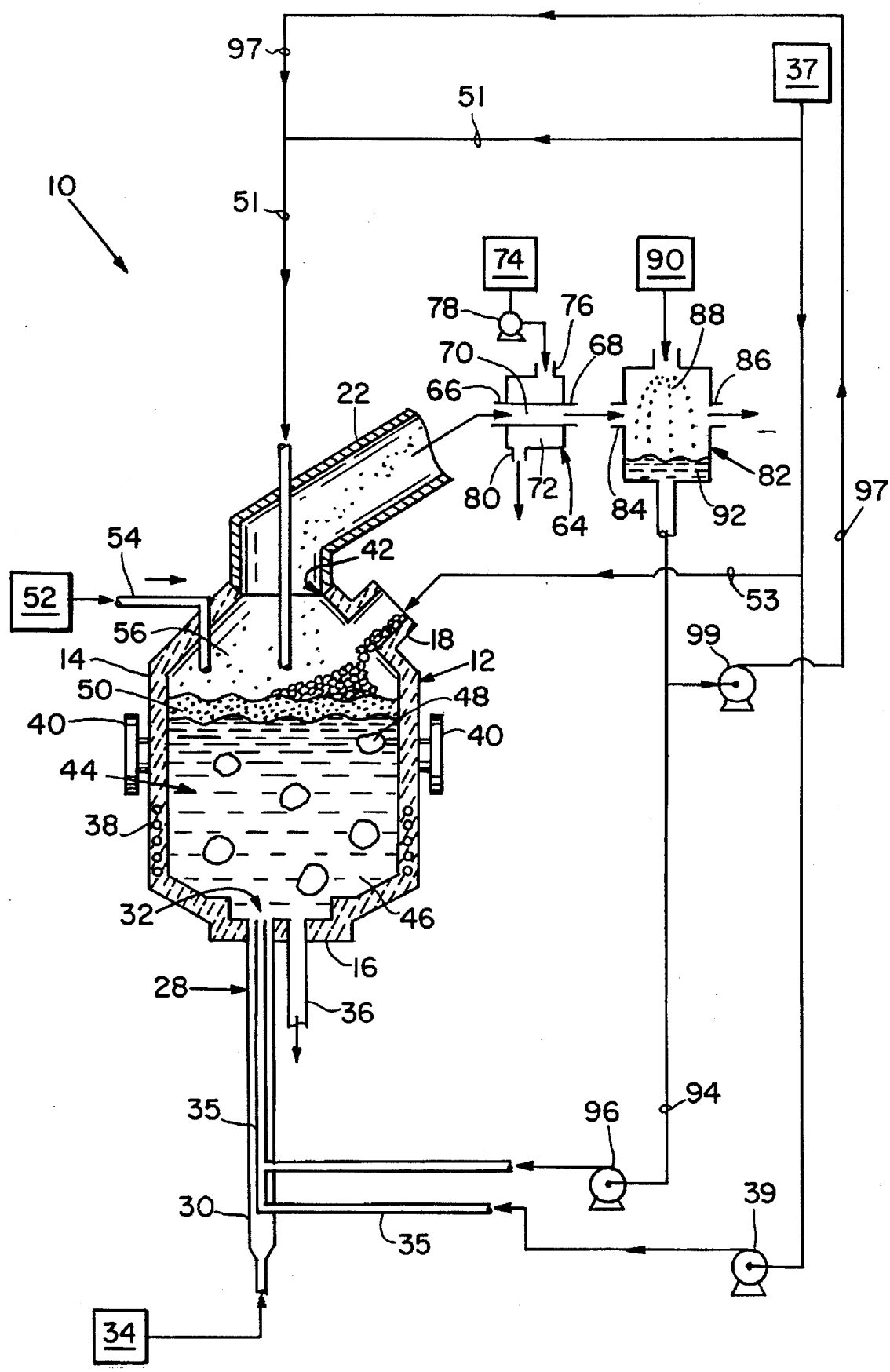

5,640,707

1

METHOD OF ORGANIC HOMOLOGATION EMPLOYING ORGANIC-CONTAINING FEEDS

BACKGROUND OF THE INVENTION

Considerable research has been conducted recently in the area of producing alkenes for use as industrial raw materials. Among the many uses of such commodity chemicals include plastics and fibers for consumption in packaging, transportation and construction industries. Of particular interest are areas of research focusing on production of alkenes, such as ethylene, which is consumed principally in the manufacture of polyethylene and substituted alkanes, such as ethylene dichloride and vinyl chloride. Ethylene is also employed in the production of ethylene oxide, ethyl benzene, ethylene dichloride, ethylene-propylene elastomers and vinyl acetate.

The primary sources of alkenes, such as ethylene, include: steam cracking of organics, such as gas oils; off-gas from fluid catalytic cracking (FCC) in oil refineries; catalytic dehydration of alcohols; and recovery for coal-derived synthesis gas. However, the worldwide demand for alkenes is extraordinary: the shortfall in worldwide supply of ethylene alone was estimated in 1991 to be about 2.3 million tons, as determined by the Chemical Economics Handbook, SRI International (1992). Further, known methods for producing alkenes have significant drawbacks. For example, all of these methods are limited to partial decomposition of organics to lower molecular weight compounds. Also, organic steam cracking, which accounts for about 100% of ethylene production in the United States, is a mature technology which is highly sensitive to process variables, such as cracking severity, residence time and organic partial pressure, as well as plant economics and price fluctuation. In addition, such processes are facing increasing environmental regulatory pressure to control systemic problems, such as leaks and failure from related equipment, and safety concerns associated with olefin cracking.

Other listed production methods have even greater limitations. The availability of FCC off-gas, for example, generally prohibits its use as an economically viable feedstock. Catalytic dehydration of alcohols are effectively limited to certain countries that have large amounts of readily available fermentation raw material. Also, known methods for production of alkenes from other sources, such as coal and coal-derived naphtha and methanol, are, at best, only marginally commercially viable.

Therefore, a need exists for an improved method of producing alkenes which significantly reduce or eliminate the above-mentioned problems.

SUMMARY OF THE INVENTION

The present invention relates to a method for organic homologation employing an organic-containing feed.

The method includes providing a reactor containing a molten metal bath. The molten metal bath includes a metal which can cause an organic component of the organic-containing feed to form a homologated organic compound. The organic-containing feed is directed into the molten metal bath. Conditions are established and maintained in the reactor to cause the organic-containing feed to form the homologated organic compound that is discharged from the molten metal bath.

The present invention includes many advantages. For example, the present invention provides good control over production of organics, such as alkenes, including ethylene.

2

Also, high yields of unsaturated organics are obtained by the present invention. The present method is a homogenous catalytic homologation process, employing solution equilibria to synthesize commercial products, such as methane, ethane and propane, from a wide variety of organic feeds, including hazardous industrial wastes. The present invention also has the ability to sustain high product quality with varying feed heterogeneity, including chemical or physical complexity. In addition, the invention provides flexibility to engineer the properties and composition of a ceramic phase generated by the method. Further, the present invention has the ability to recover and recycle volatile and nonvolatile metals.

BRIEF DESCRIPTION OF THE DRAWING

The FIGURE is a schematic representation of one embodiment of apparatus suitable for conducting the method of the invention.

DETAILED DESCRIPTION OF THE INVENTION

The features and other details of the method of the invention will now be more particularly described with reference to the accompanying figures and pointed out in the claims. It will be understood that particular embodiments of the invention are shown by way of illustration and not as limitations of the invention. The principal functions of this invention can be employed in various embodiments without departing from the scope of the invention.

The present invention generally relates to a method for producing a homologated organic compound from an organic-containing feed, such as wastes which include organic components. Processes for treating waste in molten metal baths are disclosed in U.S. Pat. Nos. 4,574,714, 5,177,304, and 4,602,574 which are incorporated herein by reference.

In one embodiment of the invention, illustrated in the FIGURE, system 10 includes reactor 12. Examples of suitable vessels include those described in U.S. Ser. No. 08/041,490 and U.S. Ser. No. 08/041,405, the teachings of which are incorporated herein by reference, and reactors which are described in U.S. Pat. No. 4,574,714, U.S. Pat. No. 5,177,304, and U.S. Pat. No. 4,602,574. Reactor 12 has an upper portion 14 and a lower portion 16. Feed inlet 18 at upper portion 14 of reactor 12 is suitable for directing feed into reactor 12. Off-gas outlet 22 extends from upper portion 14 and is suitable for conducting an off-gas out of reactor 12.

It is to be understood that the feed stream is generally introduced to molten metal bath 44 without injection of a coolant if reaction of the feed in reactor 12 is endothermic. However, tuyere 28 is dimensioned and configured for conjointly and continuously introducing a suitable feed stream and coolant into reactor 12. Tuyere 28 includes coolant tube 30 and feed inlet tube 35. Coolant tube 30 extends from coolant source 34 to reactor 12. Feed inlet tube 35 extends from feed source 37 to tuyere 28. Feed inlet tube 35 is disposed at tuyere opening 32. Pump 39 is disposed at tuyere 28 to direct a suitable feed stream from feed source 37 and through tuyere opening 32 into reactor 12. It is to be understood that an oxidant can also be fed to reactor 12 through tuyere 28 and/or other locations within reactor 12, as are taught in U.S. Pat. No. 5,191,154, the teachings of which are incorporated by reference.

It is also to be understood that more than one tuyere 28 can be disposed in reactor 12 and that concentric, or multiple concentric tuyeres, can be employed for separate introduction of the feed stream into reactor 12. Further, it is to be understood that feed can be introduced into reactor 12 by other suitable methods, such as by employing a lance, etc.

Bottom-tapping spout 36 extends from lower portion 16 and is suitable for removal of at least a portion of a molten bath from reactor 12. Additional drains can be provided as a means of continuously or intermittently removing distinct molten phases. Material can also be removed by other methods, such as are known in the art. For example, material can be removed from reactor 12 by rotating vessel 12 and employing a launder, not shown, extending from feed inlet 18. Alternatively, the launder can extend into reactor 12 through a tap hole, also not shown.

Induction coil 38 is disposed at lower portion 16 for heating reactor 12 or for initiating generation of heat within reactor 12. It is to be understood that, alternatively, reactor 12 can be heated by other suitable means, such as by using a plasma torch, electric arc, etc. Trunions 40 are disposed at reactor 12 for manipulation of reactor 12. Seal 42 is disposed between reactor 12 and off-gas outlet 22 and is suitable for allowing partial rotation of reactor 12 about trunions 40 without breaking seal 42. Alternatively, reactor 12 does not include trunions 40 or seal 42 and does not rotate.

Molten metal bath 44 is disposed within reactor 12. In one embodiment, molten metal bath 44 includes a metal which, when molten, causes at least a portion of saturated organic in the injected feed to be reformed to at least one unsaturated alkene, such as ethylene, under the operating conditions of system 10. In one embodiment, the metals of molten metal bath 44 have a melting point in the range of between about 900° C. and 1,100° C. The melting point of bath 44 is low enough to cause the organic components of the injected feed to be reformed, and subsequently discharged from bath 44, as at least one homologated organic compound.

In a particularly preferred embodiment, the operating conditions of the bath include, for example, temperatures which prevent substantial degradation of organic compounds. Also, the required residence times of the feed in the bath of molten metal are substantially shorter than are those typically employed to thermally decompose organic-containing feeds.

The thermal history of the organic compounds in the reaction zone is affected by the reaction zone temperature, residence time of the compounds in the reaction zone, and various intensive properties associated with materials in the reaction zone. The effective operating temperature is that temperature to which organic species of interest are exposed while they are in the reaction zone. This temperature is chosen so as to maximize the conditions which lead to product formation while minimizing any subsequent product degradation reactions. The effective temperature can be achieved under conditions supporting thermal equilibrium (e.g., having low temperatures in the reaction zone and relatively long residence times) or under conditions that prevent thermal equilibrium (e.g., very high temperatures in the reaction zone with relatively short residence times). For example, if the optimal product formation occurs at a substrate temperature of 900° C., this could be achieved with a liquid metal operating at 900° C. and allowing sufficient residence time for the product to reach thermal equilibrium or it could be achieved by injecting it into a high temperature reaction zone (e.g., 2000° C.) for a very short period of time, thereby providing insufficient time for the product to reach thermal equilibrium (i.e., allowing the product to exit the reaction zone at 900° C.). "Thermal equilibrium," as defined herein, means that the temperature within the reaction zone is substantially uniform. Generally, the residence time of feed components with the reaction zone is less than about five seconds. In one embodiment, the residence time is less than about 0.1 seconds. "Homologate," as that term is employed herein, means synthetic formation of an organic compound by, for example: adding at least one atom, such as at least one additional carbon, to the organic component of the feed directed into reactor 12; forming an additional hydrocarbon bond, such as by forming methane or methylene from carbon and hydrogen; or joining ends of an organic compound, such a n-hexane, to for a cyclic or aromatic compound, such as benzene.

Preferably, the carbon concentration in bath 44 is maintained at a relatively high level, such as at or near the saturation limit for carbon in the bath at the operating conditions of reactor 12. The amount of carbon in molten metal bath 44 can be controlled, for example: by the rate of introduction of the feed stream, or a carbon source such as coal, to molten metal bath 44; by controlling the rate of removal of off-gas from molten metal bath 44; by controlling system conditions, e.g., temperature, of system 10; by controlling the relative amounts of other components in molten metal bath 44; etc.

Examples of suitable metals in molten metal bath 44 include transition metals and, in particular, transition metals which have an energy gap between their ground and first excited electronic states of less than about 1.5 eV. Examples of especially suitable transition metals include rhodium, copper, etc. It is to be understood that molten bath 44 can include oxides of the molten metals. As disclosed in U.S. Pat. No. 5,177,304, the teachings of which are incorporated by reference, molten bath 44 can include more than one phase of molten metal. In one embodiment, molten bath 44 is formed of a ceramic phase which includes at least one metal oxide. In another embodiment, the ceramic phase can include at least one salt. Alternatively, a substantial portion of molten bath 44 can be of elemental metal.

Molten bath 44 can be formed by at least partially filling reactor 12 with a suitable metal. The metal is then heated to a suitable temperature by activating induction coil 38 or by other means, not shown. Optionally, two immiscible metals can be introduced to reactor 12, whereby the metals separate during melting to form two distinct molten metal phases. Alternatively, molten bath 44 includes a plurality of miscible metals including, for example, iron as one component. In one embodiment, the viscosity of at least one phase of molten bath 44 is less than about ten centipoise at the operating conditions of system 10. In another embodiment, the viscosity of at least one phase of molten bath 44 is less than about thirty poise at the operating conditions of system 10.

Suitable operating conditions of system 10 include a temperature sufficient to cause at least one metal of molten bath 44 to interact with a feed component to thereby form at least one transient organometallic intermediate. "Organometallic intermediate," as that term is used herein, means a compound or complex which is a product of an interaction between a metal and a organic component of a feed stream directed into molten bath 44. The organometallic intermediate can react with a carbon-containing component of the same feed, or a different feed, to form an homologated organic compound.

Ceramic layer 50 is disposed on molten bath 44. Ceramic layer 50 is substantially immiscible with molten bath 44. Alternatively, system 10 does not include ceramic layer 50. The solubility of carbon in ceramic layer 50 can be less than that of molten bath 44, thereby causing atomic carbon to be retained within molten bath 44. In another embodiment, ceramic layer 50 has a lower thermal conductivity than that of molten bath 44. Radiant loss of heat from molten bath 44 can thereby be reduced to significantly below the radiant heat loss from molten bath 44 when no ceramic layer 50 is present.

Examples of suitable metal oxides of ceramic layer 50 include titanium oxide ($TiO_2$), zirconium oxide ($ZrO_2$), aluminum oxide ($Al_2O_3$), magnesium oxide (MgO), calcium oxide (CaO), silica ($SiO_2$), etc. Other examples of suitable components of ceramic layer 50 include halogens, sulfur, phosphorus, heavy metals, etc. It is to be understood that ceramic layer 50 can include more than one metal oxide. Ceramic layer 50 can contain more than one phase. Typically, ceramic layer 50 is substantially fluid, thereby allowing gases to pass across ceramic layer 50 from molten bath 44.

Ceramic layer 50 can be formed by directing suitable materials, such as metals, metal oxides, halogens, sulfur, phosphorus, heavy metals, sludges, etc., from source 52 through inlet tube 54 and into molten bath 44. The materials from source 52 can be directed onto the top of molten bath 44 or injected into molten bath 44, using methods such as are well-known in the art. The materials can form other stable compounds at the operating conditions of system 10 by reaction, for example, with alkali metal cations or alkaline earth metal cations. Examples of such stable reaction products include calcium fluoride ($CaF_2$) and magnesium phosphate ($Mg(PO_4)_2$). In one embodiment, ceramic layer 50 contains about forty percent calcium oxide, about forty percent silicon dioxide, and about twenty percent aluminum oxide, and is about five inches thick.

Feed, such as an organic-containing waste in solid, liquid, or gaseous form, is directed from feed source 37 into a reaction zone within reactor 12. The reaction zone is defined to be the region in which the production formation reaction (s) occur. It can include the volume within the reactor and within attached off-gas handling equipment. The conditions supporting reaction includes liquid metal system, the gas/liquid interface, and the gas above the liquid metal which contains metal vapor and reactive metal particles and droplets (caused by entrainment).

The feed can be introduced to reactor through line 35, line 51 and/or line 53. The feed can come from a single source, such as feed source 37, or can include multiple components which are directed into molten bath 44 separately from distinct sources. The feed includes at least one organic-containing component. Examples of suitable organic-containing components include methane, ethane and propane. Examples of other hydrogen and carbon-containing feeds include "dirty" crude oil, bottoms from oil refineries, oil shales, hazardous wastes, etc. Optionally, at least two feeds can be directed into reactor 12. In one embodiment, a carbon-containing feed, such as is carbon black, is directed into reactor 12 in addition to the organic-containing feed.

The organic-containing feed and the carbon-containing feed can be directed into molten bath 44 simultaneously, such as by cofeeding them in a single stream through tuyere 28 or by injection of the organic-containing feed as a first stream and remote injection of the carbon-containing feed as a second stream. Alternatively, the organic-containing feed and the carbon-containing feed can be directed into molten bath 44 sequentially. For example, in one embodiment the organic-containing feed can be directed into molten bath 44 first, whereby a metal component of molten bath 44 interacts with the organic-containing feed to form the organometallic intermediate. The carbon-containing feed is then directed into molten bath 44 to cause carbon of the carbon-containing feed to insert into the organometallic intermediate, thereby causing an homologated organic compound to form upon elimination of the metal. The metal is restored to molten bath 44 and additional hydrogen-containing feed can be directed into molten bath 44 to repeat the sequence.

In one embodiment, the feed is injected into molten bath 44 as a component of a feed stream that also includes an inert gas component, such as argon. In one example, the feed stream can be formed by vaporizing a liquid organic feed in the presence of an inert gas. The amount of volatilized feed component in the feed stream can be, for example, in the range of between about five and forty percent, by volume.

In addition to hydrogen and carbon, the other components of the feed stream can also include other atomic constituents, such as halides, metals, etc. Metal components in the feed stream can include a metal, such as a transition metal, which can insert into the organic feed component to form the organometallic intermediate.

The feed stream directed into reactor 12 combines with molten bath 44 and can also combine with ceramic layer 50. The feed stream and coolant are directed into molten bath 44 through tuyere 28. The feed stream can also be directed into reactor 16 from feed source 37 through conduit 51. Conduit 51 discharges the feed beneath the surface of molten bath 44. Contact of the feed with molten bath 44 or ceramic layer 50 exposes the feed to conditions sufficient to form an unsaturated organic product.

Consistent with the reaction zone definition, the reaction can be carried out predominantly in the liquid metal phase, the space immediately above the condensed liquid metal phase, or in the gas space above the condensed reaction media bath, provided that sufficient concentrations of vapor, droplets, particles, etc., exist to support the necessary reaction rates. Optionally, at least a portion of molten metal bath 44 can be suspended by gas directed through tuyere 28. Suspended molten metal bath 44 can be a continuum of metal extending through a generally gaseous volume or a region of particulate molten metal suspended in a generally gaseous volume within reactor 12.

It is believed that the metal component of molten bath 44 inserts into a sigma bond of the organic-containing feed component to form an organometallic intermediate. In this oxidative addition process, the metal is formally oxidized with the resultant formation of two sigma bonds, as shown below where the organic component of the feed is methane:

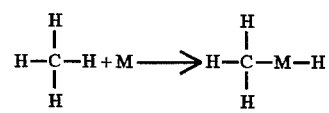

This type of addition is facilitated by metals that have relatively low energy gaps between the ground state of the metal and its first excited state. Preferably, the energy gap is less than about 1.5 eV. The insertion process is typically nearly thermoneutral because the sum of the bond energies of the two newly formed sigma bonds is comparable in magnitude to that of the sigma bond that is being broken. In a bimolecular process, involving both a carbon atom and the organometallic intermediate, it is desirable to maximize the carbon concentration in the bath.

A carbon atom derived from the carbon-containing component then inserts into a sigma bond of the organometallic intermediate to form an organic compound which includes the metal. The metal subsequently separates from the organic compound by reductive elimination, whereby at least one carbon-carbon double bond is formed, thereby forming a homologated organic compound. The organic component of the feed can be, for example, methane, which reacts with the carbon of the carbon of the carbon-containing feed to thereby form a homologated organic of higher molecular weight than the organic feed component, as shown below:

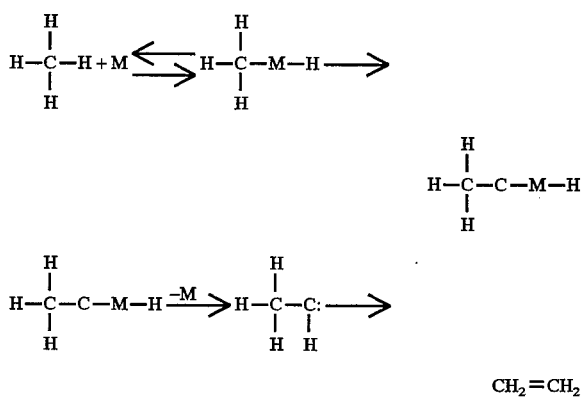

The unsaturated organic is discharged from reactor 12 as a gas.

Optionally, a feed can include a hydrogen-containing component, such as dihydrogen, and carbon-containing feed component, such as carbon black. In this embodiment, the metal can insert into a sigma bond of the dihydrogen to form a metallic dihydride. Carbon then reacts with the metal dihydride to form a homologated organic compound corresponding to methylene. Insertion of methylene into the organometallic intermediate can also result in methane homologation, as shown below:

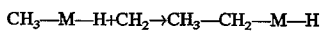

or

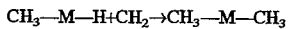

where reductive elimination results in formation of ethane.

In still another embodiment, the carbon-containing feed is a polymer, such as polyethylene, which at least partially degrades to lower molecular weight organics or to its atomic constituents in molten bath 44 before reacting with the metallic intermediate formed by combination of the metal and the organic-containing feed component.

If necessary, a coolant can be employed to cool tuyere 28. Examples of suitable coolants include steam, methane ($CH_4$), hydrogen gas ($H_2$), natural gas, etc.

Gaseous layer 56 is formed over ceramic layer 50. In one embodiment, gaseous layer 56 extends from upper portion 14 of reactor 12 through off-gas outlet 22 to scrubber 82. A reaction zone within system 10 includes molten bath 44, ceramic layer 50 and gaseous layer 56. Reactants can be introduced anywhere within the reaction zone. Gaseous layer 56 includes off-gas formed in molten bath 44 and in ceramic layer 50. The off-gas includes reaction products, such as unsaturated organics formed in molten bath 44. The off-gas can also include at least one component which has been entrained or which has been volatilized before reformation to the unsaturated organic is complete.

Off-gas formed in reactor 12 is conducted from the reaction zone through off-gas outlet 22 to heat exchanger 64.

Heat exchanger 64 can be any suitable heat exchanger for cooling off-gas discharged from reactor 12. Examples of suitable heat exchangers include water-cooled hoods, shell-and-tube heat exchangers, fluid beds, etc. Examples of off-gas components include unreacted or fragmented portions of the organic-containing feed and/or the carbon-containing feed.

The off-gas is conducted into heat exchanger 64 through heat exchanger off-gas inlet 66 and then through heat-exchanger off-gas outlet 68. Optionally, the off-gas is cooled in heat exchanger 64 by conducting the off-gas through an off-gas side 70 of heat exchanger 64 and by directing a suitable cooling medium through a medium-side 72 of heat exchanger 64. Examples of suitable cooling mediums include, for example, water, ethylene glycol, ethyl benzene, alcohols, etc. The cooling medium is directed from cooling medium source 74 through cooling medium inlet 76 of heat exchanger 64 by a suitable means, such as by use of pump 78 disposed between cooling medium source 74 and heat exchanger 64. The cooling medium is directed through the medium side 72 of heat exchanger 64, thereby cooling the off-gas, and then directed out of heat exchanger 64 through cooling medium outlet 80.

The off-gas is directed out of heat exchanger off-gas outlet 68 to a suitable separating means for exposing the off-gas to conditions sufficient to remove at least a portion of an intermediate component from the off-gas. In one illustration, the separating means is scrubber 82. The off-gas is directed through scrubber off-gas inlet 84 and then through scrubber 82 to scrubber off-gas outlet 86.

Scrubber fluid 88 is directed from scrubber fluid source 90 to scrubber 82 by a suitable means, such as by gravity or by a pump, not shown. Scrubber fluid 88 is introduced to scrubber 82 at a temperature suitable for removing at least a portion of the component from the off-gas.

It is to be understood that additional separating means can be employed to separate components from off-gas discharged from reactor 16. For example, a suitable cyclone separator, not shown, and a suitable spray drier, also not shown, can be disposed between heat exchanger 64 and scrubber 82.

Liquid composition 92 is formed by scrubbing of the off-gas with scrubber fluid 88. Liquid composition 92 is directed from scrubber 82 to reactor 12. In one embodiment, liquid composition 92 is pumped through piping 94 by pump 96 to the feed inlet tube 35. Examples of suitable pumps include a centrifugal pump, a positive displacement pump, etc. Liquid composition 92 is thereby combined with the feed for introduction into molten bath 44 through tuyere 28. In another embodiment, liquid composition 92 is directed through piping 97 by pump 99 to conduit 51. Liquid composition 92 is thereby combined with the feed stream for introduction into reactor 12 and onto molten bath 44.

At least a portion of the off-gas components are thereby returned in liquid composition 92 from the off-gas to molten bath 44. A substantial portion of the discharged feed components are then chemically reformed to homologated organics, such as ethylene. Chemical reaction of the feed components in system 10 are thereby controlled.

The invention will now be further and specifically described by the following examples. All parts and percentages are by weight unless otherwise specified.

Exemplification

A 20 lb. hot metal capacity unit was used for experimental trials, with a susceptor/crucible arrangement used for containment and heating. Various organic liquids were fed and the production of homologated organics was monitored. Feed addition was achieved by vaporizing the organic and sweeping it with an inert gas to achieve the desired inlet concentration. The gas mixture was subsequently added to the reaction zone to establish its impact on reaction homologation: carbon addition to a substrate. Substantial inert gas purges were added above the metal bath to assist in rapid product quenching. The results are summarized below.

TABLE 4

| | | Decreasing Relative Ionization Potential of Metal | | |
| --- | --- | --- | --- | --- |
| Metal | Temperature (°C.) | Feed | Benzene Concentration in off gas (%) | Toluene Concentration in off gas (%) |
| Tin | 800 | n-hexane | 0.04 | 0.03 |
| Tin | 900 | n-hexane | 0.05 | 0.04 |
| Tin | 1,000 | n-hexane | 0.07 | 0.06 |

Equivalents

Those skilled in the art will recognize, or be able to ascertain using no more than routine experimentation, many equivalents of the invention described specifically herein. Such equivalents are intended to be encompassed in the scope of the following claims.

We claim:

1. A method for organic homologation employing an organic-containing feed, comprising the steps of:
   a) providing a reactor containing a molten metal bath, said molten metal bath including a metal which can cause an organic component of the feed to form a homologated organic compound;
   b) directing the organic-containing feed into the molten metal bath at a rate which causes the carbon content of the molten bath to be at about the saturation limit of the molten metal bath; and
   c) establishing and maintaining operating conditions in said reactor to cause the organic component of the feed to homologate and form said homologated organic compound that is discharged from the molten metal bath.

2. A method of claim 1 wherein the metal provided includes a transition metal.

3. A method of claim 2 wherein the reactor which is provided contains a molten metal bath including a transition metal that has an energy gap between its ground and first excited electronic states that is less than about 1.5 eV.

4. A method of claim 1 wherein the metal bath provided includes more than one metal.

5. A method of claim 4 wherein at least two of the metals of the molten metal bath provided include transition metals that have energy gaps between their ground and first excited electronic states of less than about 1.5 eV.

6. A method of claim 1 wherein the homologated organic compound formed is unsaturated.

7. A method of claim 1 wherein at least two feeds are directed into the molten metal bath.

8. A method of claim 7 wherein the feeds are directed into the molten metal bath separately.

9. A method of claim 8 wherein the feeds are directed into the molten metal bath simultaneously.

10. A method of claim 8 wherein the feeds are directed into the molten metal bath sequentially.

11. A method of claim 10 wherein at least one of the feeds is a hydrogen-containing feed.

12. A method of claim 10 wherein at least one of the feeds is a carbon-containing feed.

13. A method for organic homologation employing an organic-containing feed, comprising the steps of:
   a) providing a reactor containing a molten metal bath, said molten metal bath including a metal which can cause a carbon black component of the feed to form a homologated organic compound;
   b) directing the organic-containing feed into the molten metal bath; and
   c) establishing and maintaining operating conditions in said reactor to cause the carbon black component of the feed to homologate and form said homologated organic compound that is discharged from the molten metal bath.

14. A method of claim 13 wherein the carbon-containing feed is directed into the molten metal bath after the organic-containing feed has been directed into the bath and wherein the organic-containing feed is directed into the molten metal bath at a rate which causes the carbon content of the metal bath to be about the saturation limit of the molten bath, whereby the carbon homologates with an organometallic intermediate of the organic-containing component to form the homologated organic compound that is discharged from the molten metal bath.

15. A method of claim 14 wherein the organometallic intermediate is divalent.

16. A method of claim 15 wherein the divalent organometallic intermediate is a metallic methylene.

17. A method of claim 16 wherein the organic-containing feed includes a saturated organic component.

18. A method of claim 17 wherein the organic-containing feed includes an alkyl organic.

19. A method of claim 18 wherein the organic-containing feed includes an alkane.

20. A method of claim 19 where the organic-containing feed includes methane.

21. A method of claim 19 wherein the organic-containing feed includes propane.

22. A method of claim 19 wherein the feed includes a first organic component and a second organic component.

23. A method of claim 22 wherein the first organic component is an alkyl organic.

24. A method of claim 23 wherein the first organic component is an alkane.

25. A method of claim 24 wherein the second organic component is an alkyl organic.

26. A method of claim 25 wherein the second organic component is an alkane.

27. A method of claim 25 wherein the second organic component is an alkene.

28. A method of claim 25 wherein the second organic component is an aryl organic compound.

29. A method of claim 2 wherein the molten metal bath provided includes copper.

30. A method of claim 1 wherein the operating conditions established and maintained in the reactor include a temperature of the molten metal bath which is less than about 1,000° C.

31. The method of claim 1 wherein said homologated organic compound is a cycloalkane.

32. The method of claim 1 wherein said homologated organic compound includes benzene.

33. The method of claim 1 wherein said homologated organic compound includes toluene.

34. A method for organic homologation employing an organic-containing feed, comprising the steps of:

a) providing a reactor containing a molten metal bath, said molten metal bath including tin and can cause an organic component of the feed to form a homologated organic compound;

b) directing the organic-containing feed into the molten metal bath; and c) establishing and maintaining operating conditions in said reactor to cause the organic component of the feed to homologate and form said homologated organic compound that is discharged from the molten metal bath.

35. The method of claim 34 wherein the organic-containing feed is directed into the molten bath at a rate which causes the carbon content of the molten bath to be at about the saturation limit of the molten bath.

36. A method for organic homologation employing an organic-containing feed, comprising the steps of:

a) providing a reactor containing a molten metal bath, said molten metal bath including rhodium and can cause an organic component of the feed to form a homologated organic compound;

b) directing the organic-containing feed into the molten metal bath; and c) establishing and maintaining operating conditions in said reactor to cause the organic component of the feed to homologate and form said homologated organic compound that is discharged from the molten metal bath.

37. The method of claim 36 wherein the organic-containing feed is directed into the molten bath at a rate which causes the carbon content of the molten bath to be at about the saturation limit of the molten bath.

38. A method for organic homologation employing an organic-containing feed, comprising the steps of:

a) providing a reactor containing a molten metal bath, said molten metal bath including a metal which can cause an organic component of the feed to form a homologated organic compound;

b) directing the organic-containing feed into the molten metal bath; and c) establishing and maintaining operating conditions at a temperature between about 900° and 1100 ° C. in the molten bath to cause the organic component of the feed to homologate and form said homologated organic compound that is discharged from the molten metal bath.

39. The method of claim 38 wherein the organic-containing feed is directed into the molten metal bath at a rate which causes the carbon content of the molten bath to be at about the saturation limit of the molten bath.

* * * * *